United States Patent
Lee et al.

(10) Patent No.: US 6,723,566 B2
(45) Date of Patent: Apr. 20, 2004

(54) PD/NI-WO₃ ANODIC DOUBLE LAYER GASOCHROMIC DEVICE

(75) Inventors: Se-Hee Lee, Lakewood, CO (US); C. Edwin Tracy, Golden, CO (US); J. Roland Pitts, Lakewood, CO (US); Ping Liu, Denver, CO (US)

(73) Assignee: Midwest Research Institute, Kansas City, MO (US)

( * ) Notice: Subject to any disclaimer, the term of this patent is extended or adjusted under 35 U.S.C. 154(b) by 0 days.

(21) Appl. No.: 10/240,020

(22) PCT Filed: May 5, 2001

(86) PCT No.: PCT/US01/14381

§ 371 (c)(1),
(2), (4) Date: Jan. 29, 2003

(87) PCT Pub. No.: WO01/86258

PCT Pub. Date: Nov. 15, 2001

(65) Prior Publication Data

US 2004/0037745 A1 Feb. 26, 2004

Related U.S. Application Data

(60) Provisional application No. 60/202,501, filed on May 5, 2000.

(51) Int. Cl.⁷ ............................................. G01N 21/78
(52) U.S. Cl. ..................... 436/144; 436/167; 422/86; 422/91
(58) Field of Search ................. 436/144, 164, 436/167; 422/86, 87, 91

(56) References Cited

U.S. PATENT DOCUMENTS

| 4,661,320 A | 4/1987 | Ito et al. |
| 4,976,991 A | * 12/1990 | Ammende et al. ........... 427/125 |
| 5,342,701 A | * 8/1994 | Miremadi et al. .......... 428/701 |
| 5,405,583 A | 4/1995 | Goswami et al. |
| 6,535,658 B1 | * 3/2003 | Mendoza et al. ............. 385/12 |

FOREIGN PATENT DOCUMENTS

JP       60211348 A  * 10/1985  .......... G01N/27/12

OTHER PUBLICATIONS

Patent Abstracts of Japan, vol. 012, No. 136(P–694), Apr. 26, 1988 & JP 62 257047 A(Hochiki Corp.), Nov. 9, 1987, abstract.

Shen, P.K. et al., "The Performance of Electrochromic Tungsten Trioxide Films Doped with Cobalt or Nickel" Journal of the Electrochemical Society, Electrochemical Society, Manchester, New Hampshire, US, vol. 138, No. 9, Sep. 1, 1991, pp. 2778–2783, XP000248209.

Lee, S–H. et al., "Characterization of Ni–W Oxide Thin Film Electrodes", Solid State Ionics, North Holland Pub. Co. Amsterdam, NL, vol. 109, No. 3–4, Jun. 2, 1998, pp. 303–310, XP004124974.

* cited by examiner

Primary Examiner—Jeffrey R. Snay
(74) Attorney, Agent, or Firm—Paul J. White

(57) ABSTRACT

An anodic double layer gasochromic sensor structure for optical detection of hydrogen in improved response time and with improved optical absorption real time constants, comprising: a glass substrate; a tungsten-doped nickel oxide layer coated on the glass substrate; and a palladium layer coated on the tungsten-doped nickel oxide layer.

10 Claims, 2 Drawing Sheets

PD/NI-WO₃ ANODIC DOUBLE LAYER GASOCHROMIC DEVICE

This application claims priority from U.S. Provisional Application Serial No. 60/202,501 filed May 5, 2000.

CONTRACTED ORIGIN OF THE INVENTION

The United States Government has rights in this invention under Contract No. DE-AC36-99GO10337 between the United States Department of Energy and the National Renewable Energy Laboratory, a division of the Midwest Research Institute.

TECHNICAL FIELD

The invention relates to a Pd/Ni $WO_3$ (palladium/tungsten-doped nickel oxide) anodic double layer gasochromic device in which the palladium layer functions as a catalyst material that facilitates reaction with hydrogen gas. The hydrogen gas is disassociated on the Pd catalyst into H atoms, which diffuse into the Ni—$WO_3$ film. The Ni—$WO_3$ thin film exhibits an anodic coloration with $H^+$ or $Li^+$ insertion. The Ni—$WO_3$ thin film is more stable than $WO_3$ films in air, due to the fact that Ni oxide based materials, unlike $WO_3$, forms a hydroxide upon absorption of water vapor. Even after forming the hydroxide, the Ni—W hydroxide thin film still shows a strong color change. By use of the gasochromic response upon exposure to hydrogen gas, hydrogen gas monitoring of the anodic double layer device of the invention can be detected via optical detection schemes such as a fiber-optic type $H_2$ sensor.

1. Background Art

Hydrogen is a plentiful, clean, non-polluting fuel. Hydrogen is currently used in many industries, and the US demand for hydrogen is approximately 140 billion cubic feet per year and growing. However, hydrogen is explosive at 4% in air. Therefore, it is critical to measure, monitor and control hydrogen wherever it is used.

In the gasochromic art where sensors and measurement instrumentation for hydrogen gases detect and/or measure hydrogen, typically there is required a portable sensing device, a kit (where hydrogen gas detection and/or measurement is required in existing equipment), and sensor heads installed at points where hydrogen leaks are possible, or where monitoring is necessary (i.e., in internal combustion engines which operate using hydrogen as a fuel).

The problems associated with current $H_2$ gasochromic devices are that these devices are not of adequate durability in that they degrade quickly with cycling and time, are too moisture sensitive, and react too slowly in response to the presence of $H_2$ to produce an optical absorption change with a lengthy time constant in the vicinity of 30 seconds.

2. Description of the Related Art

At present, optical detection of $H_2$ is widely accomplished through the use of Pd/$WO_3$ hydrogen detecting gasochromic devices. However, several problems or drawbacks are associated with the use of Pd/$WO_3$ hydrogen detecting gasochromic devices. These problems are: they are of inadequate durability; they respond slowly to the presence of $H_2$; and there is a conflicting cathodic-anodic optical response that results in a weak color change.

Inadequate durability problems are occasioned by the fact that the Pd/$WO_3$ hydrogen detecting gasochromic device degrades quickly with cycling and time, and is unduly moisture sensitive.

The slow response of the Pd/$WO_3$ hydrogen detecting gasochromic device in the presence of a $H_2$ leak is due to the hydrogen reaction in $H_xWO_3$ which produces a slow optical absorption change within a lengthy room temperature time constant of about 30 seconds.

Also, there is a conflicting optical response upon detection of $H_2$ by the Pd/$WO_3$ gasochromic device due to the fact that the $WO_3$ exhibits a cathodic response and the Pd exhibits an opposite anodic response.

3. Disclosure of Invention

One object of the present invention is to provide an anodic double layer $H_2$ detecting gasochromic device of improved durability that shows little degradation with cycling and time.

A further object of the present invention is to provide an anodic double layer $H_2$ detecting gasochromic device that responds more swiftly to detection of $H_2$ gas by producing faster optical absorption change within a room temperature time constant of about 10 seconds.

Another object of the present invention is to provide an anodic double layer $H_2$ detecting gasochromic device comprising complementary coloring layers in which both of the layers consist of an anodic coloration material.

In general, the invention is accomplished by providing a palladium/tungsten-doped nickel oxide anodic double layer gasochromic device in which, a Ni—$WO_3$ thin film is prepared on a glass substrate by reactive sputtering. Thereafter, a palladium layer is evaporated onto the Ni—$WO_3$ thin film. The palladium layer serves as a catalyst material that facilitates reaction with hydrogen gas. That is, the hydrogen gas is dissociated on the Pd catalyst into H atoms, which readily diffuse into the Ni—$WO_3$ film. The Ni—$WO_3$ thin film exhibits an anodic coloration with insertion of either $H^+$ or $Li^+$.

The Ni—$WO_3$ thin films are more stable than $WO_3$ films in air due to the fact that Ni oxide based materials, unlike $WO_3$, form a hydroxide upon absorption of water vapor. Even after formation of the hydroxide, Ni—W hydroxide thin films still show a strong color change. By use of this gasochromic response upon exposure to hydrogen gas, hydrogen gas can be monitored via optical detection schemes such as fiber-optic type $H_2$ sensors.

BEST MODE FOR CARRYING OUT THE INVENTION

Due to the fact that Pd/$WO_3$ sensors are encumbered by inadequate durability, slow response time, and conflicting optical responses upon detecting $H_2$, a need exists in the interest of safety to provide $H_2$ sensors of improved durability, faster response time, and a non-conflicting optical response when detecting hydrogen, which is explosive at 4% in air.

The Pd/WO$_3$ sensor is of inadequate durability because it degrades quickly with cycling and time and is unduly moisture sensitive. Further, the slow response time of Pd/WO$_3$ sensors is due to hydrogen reaction in H$_x$WO$_3$ which produces optical absorption change with a room temperature time constant of 30 seconds. Further still, the Pd/WO$_3$ sensor exhibits a conflicting optical response due to the fact that the WO$_3$ undergoes a cathodic response and the Pd exhibits an anodic response.

The improved gasochromic device of the invention is obtained by preparing Ni—WO$_3$ thin film on a glass substrate by reactive sputtering. Thereafter, a palladium layer is evaporated onto the Ni—WO$_3$ thin film. The palladium layer is used as a catalyst material to facilitate reaction with hydrogen. When the palladium layer reacts with hydrogen, hydrogen gas is dissociated on the Pd catalyst into H atoms, which readily diffuse into the Ni—WO$_3$ film.

The Ni—WO$_3$ thin films show an anodic coloration upon insertion of H$^+$ or Li$^+$, unlike WO$_3$, as follows:

$$Ni^{3+} \leftrightarrow Ni^{2+}.$$

The Pd also shows anodic coloration in accordance with the following equation:

$$Pd \leftrightarrow PdH_x.$$

It has been found that the Ni—WO$_3$ thin films are much more stable than WO$_3$ in air because the nickel oxide based materials, unlike the WO$_3$ tend to form a hydroxide with absorption of water vapor, and even after forming the hydroxide, the Ni—W hydroxide thin film still shows a strong color change.

Figure 1:
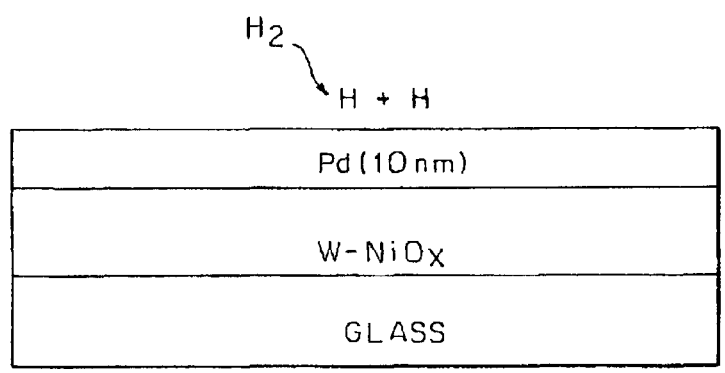
FIG. 1 depicts gasochromism of a Pd/EC oxide $H_2$ device in which hydrogen gas is disassociated on the Pd catalyst into H atoms.

Reference is now made to FIG. 1, which shows the gasochromism of a palladium electrochromic (EC) oxide H$_2$ device. In this device, hydrogen gas is dissociated on the Pd catalyst into H atoms, and the H atoms diffuse into the WO$_3$ layer in accordance with the following formula:

$$xH^+ + xe^- + WO_3 = H_xWO_3,$$

where W$^{6+} \rightarrow$ W$^{5+}$

Figure 2:
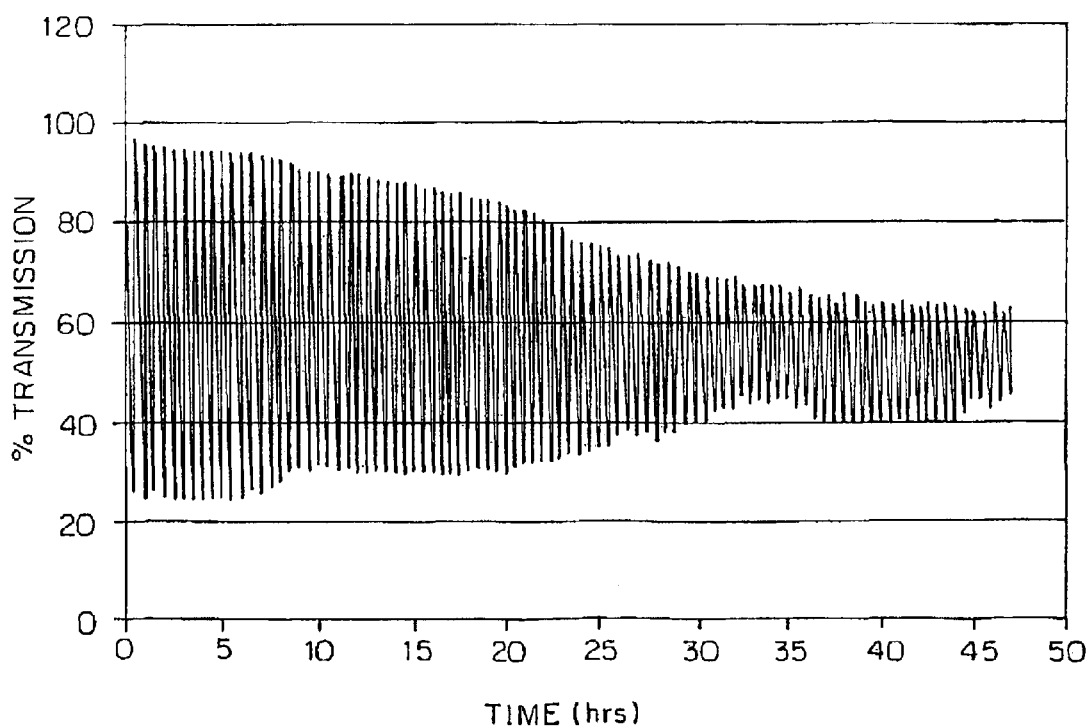
FIG. 2 is a chart showing percent transmission versus time for cycling results of a prior art Pd/$WO_3$ hydrogen sensor device.

FIG. 2 is a graph showing percent relative transmission versus time for cycling results of the Pd/WO$_3$ gasochromic hydrogen sensing device.

Figure 3:
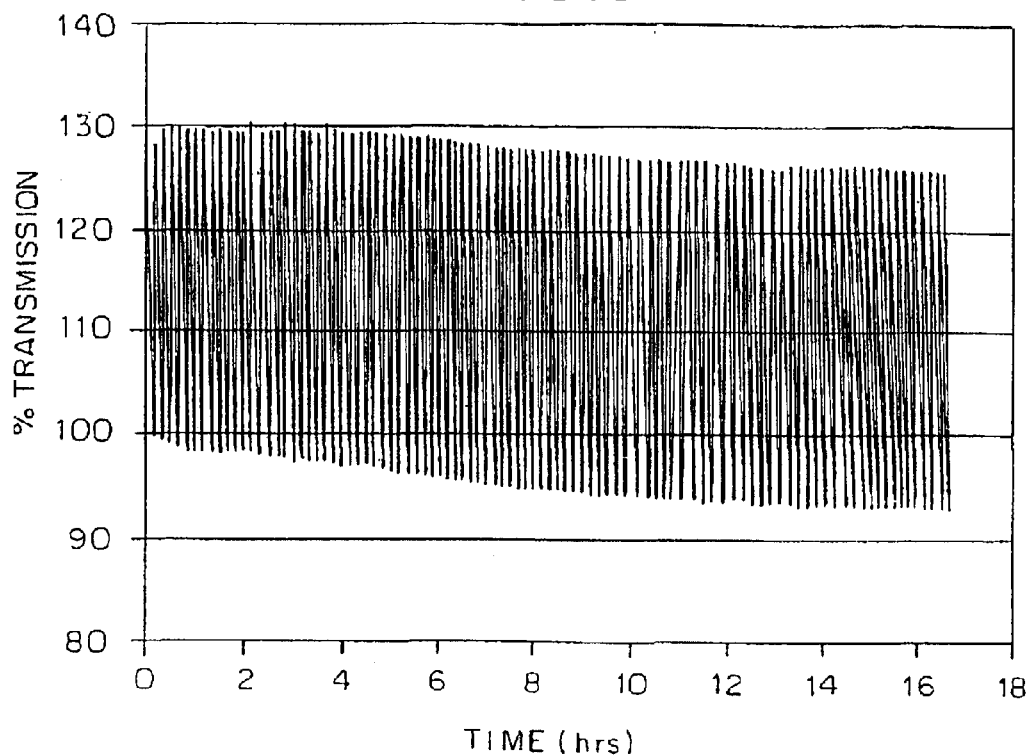
FIG. 3 is a graph showing percent transmission versus time for cycling results of the PdNi—$WO_3$ hydrogen sensor of the invention.

FIG. 3 is a graph showing percent relative transmission versus time for cycling results of the PdNi—WO$_3$ anodic double layer hydrogen sensor of the invention.

The PdNi—WO$_3$ sensor shows little degradation with cycling and time. Further, the hydrogen reaction in the Pd/Ni—WO$_3$ produces a fast response optical absorption change with a room temperature time constant of just 10 seconds, because the Ni—WO$_3$ thin film shows anodic coloration with H$^+$ insertion (unlike WO$_3$), per:

$$Ni^{3+}(color) \leftrightarrow Ni^{2+}(transparent)$$

Because the Pd also shows anodic coloration per Pd$\leftrightarrow$PdH$_x$, there is very strong color change upon detection of H$_2$ as there is no conflicting cathodic and anodic response as in the case of the Pd/WO$_3$ gasochromic device. This strong color change is further aided by the fact that, while WO$_3$ films are sensitive to air (and the moisture therein), the Ni—WO$_3$ films form a hydroxide with air as follows:

$$Ni-W\ oxide \rightarrow NiW(OH)_2,$$

and due to the fact that nickel hydroxide is moisture insensitive, it does not off-set the strong color change of the anodic coloration's due to the nickel oxide and palladium complementary coloring layers.

Figure 4:
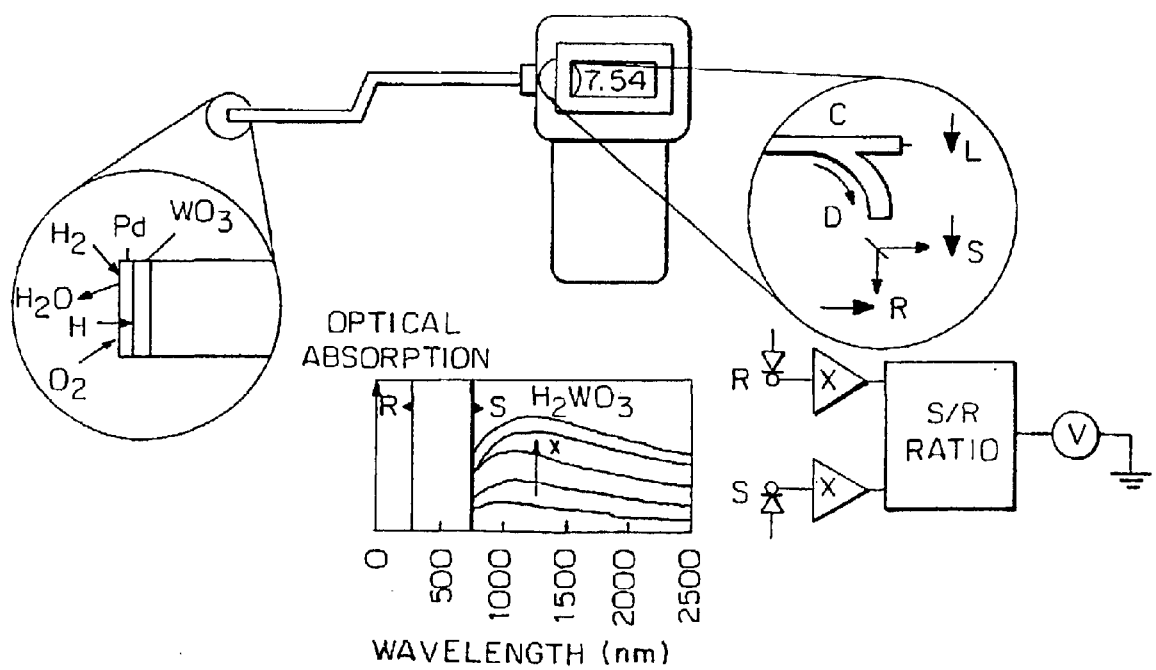
FIG. 4 is a diagram showing a fiber-optic $H_2$ sensor in which the gasochromic response upon exposure to $H_2$ is measured.

Reference is now made to FIG. 4 in which a diagram shows a fiber-optic H$_2$ sensor in which the gasochromic response upon exposure to H$_2$ is measured The exploded or enlarged sectional view shows the reaction caused by detection of the presence of hydrogen by the palladium catalyst layer and the diffusion of the H$^+$ into the WO$_3$ layer in accordance with the following formula:

$$4H_2 + O_2 + nWO_3 \rightleftharpoons nH_{4/n}WO_3 + 2H_2O$$

In FIG. 4, another exploded or sectional view of the meter measurement for hydrogen detection comprises the following key designated components:

C-Coupler, L-LED, D-Dichroic Mirror, S-Signal photodiode, R-Reference photodiode.

The optical absorption in. wavelength based upon the amount of hydrogen is shown in nm.

The invention device applied to an optical fiber comprises placing the Ni—WO$_3$ thin film coated with the Pd layer onto an optical fiber. The adaption of the invention device to a fiberoptic sensor is important because:

1) It allows elimination of an ignition energy source at the leak site, thereby limiting the risk of an explosion;
2) The fiber-optic signal transmission is immune to electromagnetic interference; and
3) The sensor and opto-electronic are very economical to match-up.

While the invention Pd/Ni—WO$_3$ device is primarily for purposes of sensing H$_2$ due to its improved kinetics and durability in air, it is to be emphasized that the invention works equally as well in that it also exhibits anodic coloration upon insertion of Li$^+$. Further, the hydrogen sensing oxide material, in addition to being. Ni—WO$_3$ may be Ni—Ta oxide to obtain reversible coloration$\neq$bleaching.

What is claimed is:

1. An anodic double layer gasochromic sensor structure for optical detection of hydrogen in improved response time and with improved optical absorption real time constants, comprising:
    a substrate;
    a nickel-tungsten oxide layer coated on said substrate; and
    a palladium layer coated on said nickel-tungsten oxide layer.

2. The anodic double layer gasochromic sensor structure of claim 1 wherein said palladium layer is 10 nm.

3. The anodic double layer gasochromic sensor structure of claim 2 wherein said tungsten-doped nickel oxide layer and said palladium layer comprise anodic coloration materials.

4. A method of preparing an improved gasochromic sensor for optical detection of hydrogen with improved response time and improved optical absorption real time constants, comprising:
    providing a substrate;
    depositing a tungsten-doped nickel oxide layer on said substrate; and
    depositing a palladium layer onto said tungsten-doped nickel oxide layer.

5. The method of claim 4 wherein said tungsten-doped nickel oxide layer is deposited by reactive sputtering.

6. The method of claim 5 wherein said absorption change is within a real time constant of about 10 seconds.

7. The method of claim 6 wherein said palladium layer is evaporated onto said tungsten-doped nickel oxide layer.

8. The method of claim 7 wherein said substrate is an optical fiber and said tungsten-doped nickel oxide on which said palladium layer is coated is placed onto said optical fiber.

9. An improved method of optically detecting hydrogen with improved response time and improved optical absorption real time constants, comprising:

subjecting an anodic double layer gasochromic sensor structure comprising a substrate, a layer of tungsten-doped nickel oxide coated on said substrate, and a layer of palladium coated on said tungsten-doped nickel oxide to an environment comprising hydrogen gas to cause a reaction of palladium and hydrogen to dissociate said hydrogen gas into H atoms on said palladium and to diffuse said H atoms into a W—NiO$_x$ film to cause an anodic coloration in accordance with the equation:

$$Ni^{3+} \leftrightarrow Ni^{2+}$$

and to cause an anodic coloration in accordance with the equation:

$$Pd \leftrightarrow PdH_x.$$

10. A method of optically detecting hydrogen gas with improved response time and improved optical adsorption real time constants that eliminates an ignition energy source at the leak site, thereby limiting the risk of explosion, comprising:

subjecting an anodic double layer gasochromic sensor structure comprising a optical fiber, a layer of tungsten-doped nickel oxide coated on said optical fiber, and a layer of palladium coated on said tungsten-doped nickel oxide to an environment comprising hydrogen gas to cause a reaction of palladium and hydrogen to dissociate said hydrogen gas into H atoms on said palladium and to diffuse said H atoms into a W—NiO$_x$ film to cause an anodic coloration in accordance with the equation:

$$Ni^{3+} \leftrightarrow Ni^{2+}$$

said layer of tungsten-doped nickel oxide coated with palladium being placed within an optical fiber.

* * * * *